(12) United States Patent
Hakoshima

(10) Patent No.: US 11,241,152 B2
(45) Date of Patent: Feb. 8, 2022

(54) EVALUATION DEVICE, EVALUATION METHOD, AND NON-TRANSITORY STORAGE MEDIUM

(71) Applicant: JVC KENWOOD Corporation, Yokohama (JP)

(72) Inventor: Shuji Hakoshima, Yokohama (JP)

(73) Assignee: JVC KENWOOD Corporation, Yokohama (JP)

( * ) Notice: Subject to any disclaimer, the term of this patent is extended or adjusted under 35 U.S.C. 154(b) by 281 days.

(21) Appl. No.: 16/270,616

(22) Filed: Feb. 8, 2019

(65) Prior Publication Data
US 2019/0261850 A1 Aug. 29, 2019

(30) Foreign Application Priority Data
Feb. 28, 2018 (JP) .............................. JP2018-035344

(51) Int. Cl.
  *A61B 3/02* (2006.01)
  *A61B 3/032* (2006.01)
  *A61B 3/00* (2006.01)
  *A61B 3/14* (2006.01)
  *A61B 3/113* (2006.01)

(52) U.S. Cl.
  CPC ............ *A61B 3/032* (2013.01); *A61B 3/0025* (2013.01); *A61B 3/0041* (2013.01); *A61B 3/0091* (2013.01); *A61B 3/113* (2013.01); *A61B 3/14* (2013.01)

(58) Field of Classification Search
  CPC ....... A61B 3/032; A61B 3/113; A61B 3/0041; A61B 3/14; A61B 3/0025; A61B 3/0091; A61B 3/024

USPC ......................................... 351/209, 237–239
See application file for complete search history.

(56) References Cited

U.S. PATENT DOCUMENTS

2017/0245753 A1* 8/2017 Donaldson ............. A61B 3/113
2017/0360295 A1* 12/2017 Oz ........................ G06K 9/3233
2020/0329959 A1* 10/2020 Goldberg ............. A61B 3/0033

FOREIGN PATENT DOCUMENTS

| JP | 2011-161122 | 8/2011 |
| JP | 2011161122 A | * 8/2011 |
| JP | 2016-193067 | 11/2016 |

* cited by examiner

*Primary Examiner* — Mahidere S Sahle
(74) *Attorney, Agent, or Firm* — Amin, Turocy & Watson, LLP

(57) ABSTRACT

An evaluation device includes: a display screen configured to displays images; a gaze point detection unit configured to detect a position of a gaze point of an examinee who observes the display screen; a display controller configured to display an indicator at an offset position having a predetermined relative positional relationship with the gaze point on the display screen based on a detection result of the position of the gaze point; an arithmetic unit configured to determine whether the examinee has recognized the indicator; and an evaluation unit configured to evaluate a visual function of the examinee based on a determination result from the arithmetic unit, wherein the arithmetic unit is further configured to determine that the examinee has recognized the indicator when the gaze point moves toward the indicator and thus the offset position is located outside the display screen.

4 Claims, 12 Drawing Sheets

EVALUATION DEVICE, EVALUATION METHOD, AND NON-TRANSITORY STORAGE MEDIUM

CROSS-REFERENCE TO RELATED APPLICATION

This application claims priority from Japanese Application No. 2018-035344, filed on Feb. 28, 2018, the contents of which are incorporated by reference herein in its entirety.

FIELD

The present application relates to an evaluation device, an evaluation method, and a non-transitory storage medium.

BACKGROUND

As an evaluation method of evaluating whether or not there is a visual field deficiency in a retina, for example, a method of causing an examinee to gaze at a point and examining whether the examinee has recognized an indicator presented around the point is known (for example, Japanese Laid-open Patent Publication No. 2011-161122 A).

In the method disclosed in Japanese Laid-open Patent Publication No. 2011-161122 A, a configuration in which an indicator is presented only when an examinee gazes at a presented indicator is not employed. Accordingly, it is difficult to determine whether an examinee can recognize an indicator with peripheral vision and it is also difficult to accurately evaluate whether or not there is a visual field deficiency. Accordingly, there is demand for a technique capable of performing evaluation with higher accuracy.

SUMMARY

An evaluation device, an evaluation method, and a non-transitory storage medium are disclosed.

According to one aspect, there is provided an evaluation device comprising: a display screen configured to displays images; a gaze point detection unit configured to detect a position of a gaze point of an examinee who observes the display screen; a display controller configured to display an indicator at an offset position having a predetermined relative positional relationship with the gaze point on the display screen based on a detection result of the position of the gaze point; an arithmetic unit configured to determine whether the examinee has recognized the indicator; and an evaluation unit configured to evaluate a visual function of the examinee based on a determination result from the arithmetic unit, wherein the arithmetic unit is further configured to determine that the examinee has recognized the indicator when the gaze point moves toward the indicator and thus the offset position is located outside the display screen.

According to one aspect, there is provided an evaluation method comprising: detecting a position of a gaze point of an examinee who observes a display screen that displays images; displaying an indicator at an offset position having a predetermined relative positional relationship with the gaze point on the display screen based on a detection result of the position of the gaze point; determining whether the examinee has recognized the indicator; evaluating a visual function of the examinee based on a determination result of the recognition of the indicator; and determining that the examinee has recognized the indicator when the gaze point moves toward the indicator and thus the offset position is located outside the display screen.

According to one aspect, there is provided a non-transitory storage medium that store an evaluation program causing a computer to perform: detecting a position of a gaze point of an examinee who observes a display screen that displays images; displaying an indicator at an offset position having a predetermined relative positional relationship with the gaze point on the display screen based on a detection result of the position of the gaze point; determining whether the examinee has recognized the indicator; evaluating a visual function of the examinee based on a determination result of the recognition of the indicator; and determining that the examinee has recognized the indicator when the gaze point moves toward the indicator and thus the offset position is located outside the display screen.

The above and other objects, features, advantages and technical and industrial significance of this application will be better understood by reading the following detailed description of presently preferred embodiments of the application, when considered in connection with the accompanying drawings.

DETAILED DESCRIPTION OF THE PREFERRED EMBODIMENTS

Hereinafter, embodiments of an evaluation device, an evaluation method, and a non-transitory storage medium according to the application will be described with reference to the accompanying drawings. Incidentally, the application is not limited to the embodiments. Further, elements in the following embodiments include elements which can be easily replaced by those skilled in the art or substantially the same elements.

In the following description, a three-dimensional global coordinate system is set and positional relationships between the elements are described therein. A direction which is parallel to a first axis of a predetermined plane is defined as an X-axis direction, a direction which is parallel to a second axis of the predetermined plane perpendicular to the first axis is defined as a Y-axis direction, and a direction which is parallel to a third axis perpendicular to the first axis and the second axis is defined as a Z-axis direction. The predetermined plane includes an XY plane.

Line-of-Sight Detecting Device

Figure 1:
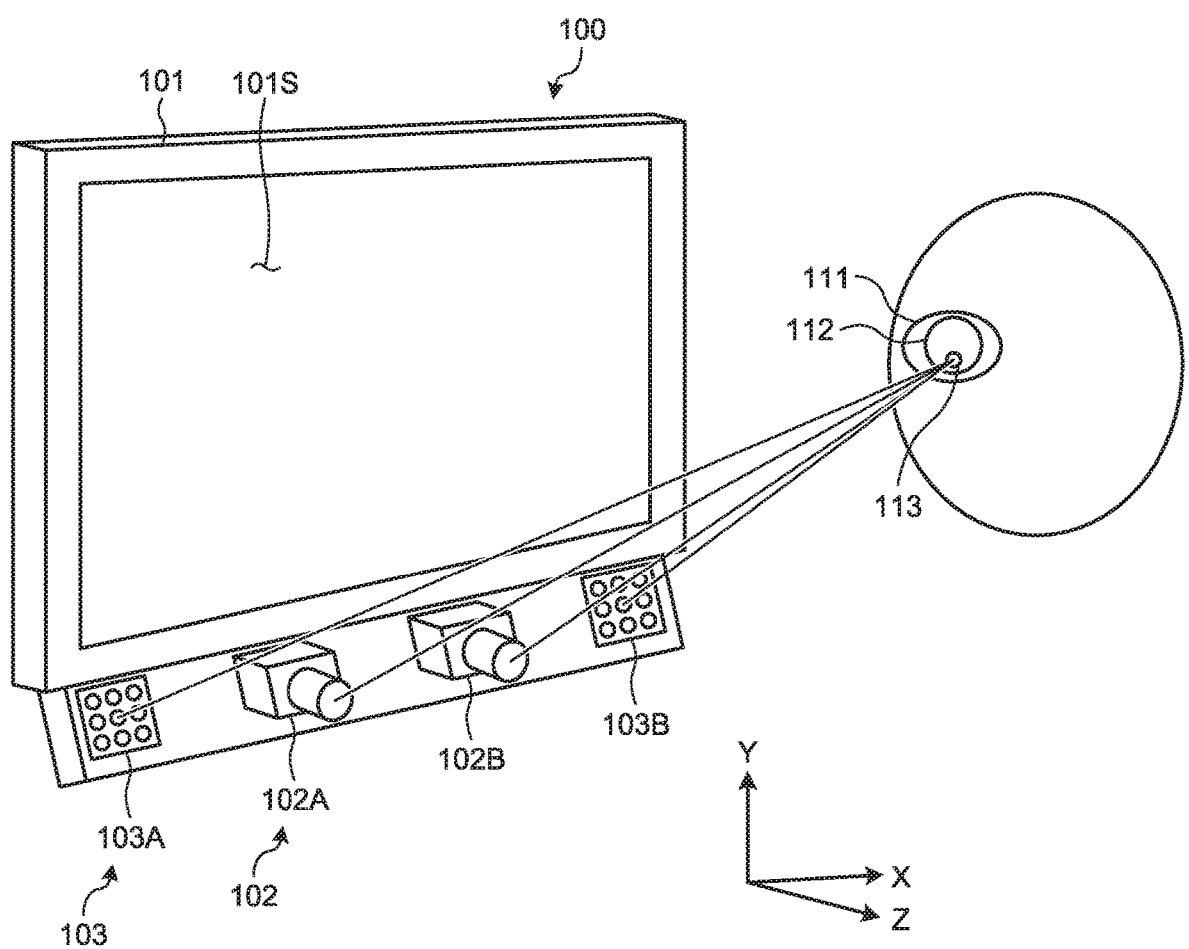
FIG. 1 is a perspective view schematically illustrating an example of a line-of-sight detecting device according to a present embodiment.

FIG. 1 is a perspective view schematically illustrating an example of a line-of-sight detecting device 100 according to a first embodiment. The line-of-sight detecting device 100 is used as an evaluation device that evaluates whether or not there is a visual field deficiency due to glaucoma or the like as a visual function of an examinee. As illustrated in FIG. 1, the line-of-sight detecting device 100 includes a display device 101, a stereo camera device 102, an illumination device 103, and an examinee input unit 70.

The display device 101 includes a flat panel display such as a liquid crystal display (LCD) or an organic electroluminescence (EL) display (OLED). In the present embodiment, the display device 101 includes a display screen 101S. The display screen 101S displays an image. In the present embodiment, the display screen 101S displays, for example, an indicator for evaluating a visual function of an examinee. The display screen 101S is substantially parallel to the XY plane. The X-axis direction is a horizontal direction of the display screen 101S, the Y-axis direction is a vertical direction of the display screen 101S, and the Z-axis direction is a depth direction which is perpendicular to the display screen 101S.

The stereo camera device 102 includes a first camera 102A and a second camera 102B. The stereo camera device 102 is disposed below the display screen 101S of the display device 101. The first camera 102A and the second camera 102B are disposed in the X-axis direction. The first camera 102A is disposed on the −X side with respect to the second camera 102B. Each of the first camera 102A and the second camera 102B includes an infrared camera and includes, for example, an optical system that can transmit near-infrared light with a wavelength of 850 [nm] and an imaging element that can receive the infrared light.

The illumination device 103 includes a first light source 103A and a second light source 103B. The illumination device 103 is disposed below the display screen 101S of the display device 101. The first light source 103A and the second light source 103B are disposed in the X-axis direction. The first light source 103A is disposed on the −X side with respect to the first camera 102A. The second light source 103B is disposed on the +X side with respect to the second camera 102B. Each of the first light source 103A and the second light source 103B includes a light emitting diode (LED) as the light source and can emit, for example, near-infrared light with a wavelength of 850 [nm]. Incidentally, the first light source 103A and the second light source 103B may be disposed between the first camera 102A and the second camera 102B.

The illumination device 103 emits near-infrared light which is detection light and illuminates an eyeball 111 of an examinee. The stereo camera device 102 images the eyeball 111 with the second camera 102B when the detection light emitted from the first light source 103A is applied to the eyeball 111, and images the eyeball 111 with the first camera 102A when the detection light emitted from the second light source 103B is applied to the eyeball 111.

A frame synchronization signal is output from at least one of the first camera 102A and the second camera 102B. The first light source 103A and the second light source 103B emit detection light based on the frame synchronization signal. The first camera 102A acquires image data of the eyeball 111 when the detection light emitted from the second light source 103B is applied to the eyeball 111. The second camera 102B acquires image data of the eyeball 111 when the detection light emitted from the first light source 103A is applied to the eyeball 111.

When the detection light is applied to the eyeball 111, a part of the detection light is reflected by a pupil 112 and the reflected light from the pupil 112 is incident on the stereo camera device 102. Further, when the detection light is applied to the eyeball 111, a corneal reflex image 113 which is a virtual image of the cornea is formed in the eyeball 111 and light from the corneal reflex image 113 is incident on the stereo camera device 102.

By appropriately setting relative positions between the first camera 102A, the second camera 102B, the first light source 103A, and the second light source 103B, intensity of the light incident on the stereo camera device 102 from the pupil 112 decreases and intensity of the light incident on the stereo camera device 102 from the corneal reflex image 113 increases. That is, an image of the pupil 112 acquired by the stereo camera device 102 has low luminance and an image of the corneal reflex image 113 has high luminance. The stereo camera device 102 can detect the position of the pupil 112 and the position of the corneal reflex image 113 based on the luminance of the acquired image.

Figure 2:
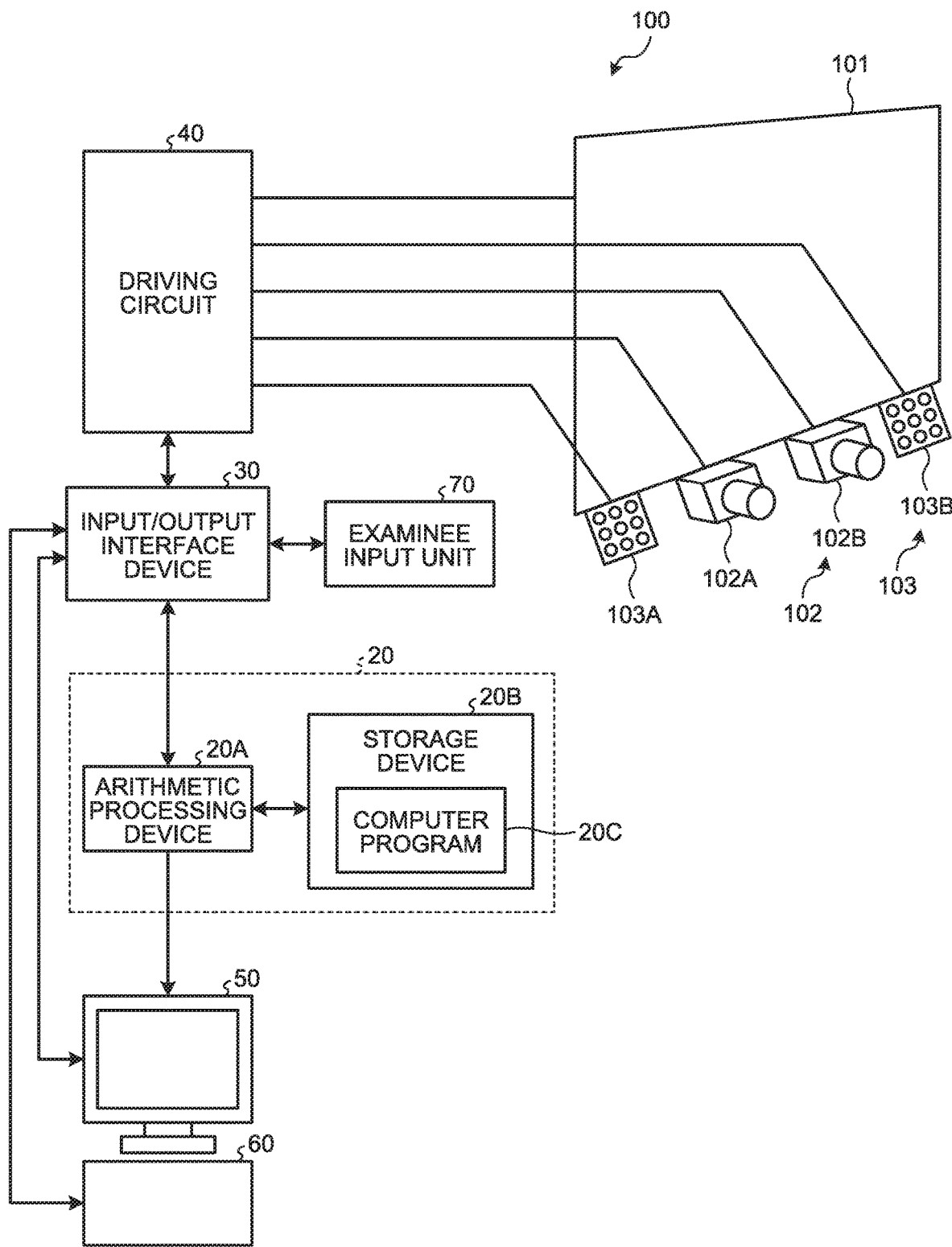
FIG. 2 is a diagram illustrating an example of a hardware configuration of the line-of-sight detecting device according to the embodiment.

FIG. 2 is a diagram illustrating an example of a hardware configuration of the line-of-sight detecting device 100 according to the present embodiment. As illustrated in FIG. 2, the line-of-sight detecting device 100 includes the display device 101, the stereo camera device 102, the illumination device 103, a computer system 20, an input/output interface device 30, a driving circuit 40, an output device 50, an input device 60, and the examinee input unit 70.

The computer system 20, the driving circuit 40, the output device 50, the input device 60, and the examinee input unit 70 perform data communication with each other via the input/output interface device 30. The computer system 20 includes an arithmetic processing device 20A and a storage device 20B. The arithmetic processing device 20A includes a microprocessor such as a central processing unit (CPU). The storage device 20B includes a memory or a storage such as a read only memory (ROM) and a random access memory (RAM). The arithmetic processing device 20A performs an arithmetic process in accordance with a computer program 20C stored in the storage device 20B.

The driving circuit 40 generates drive signals and outputs the drive signals to the display device 101, the stereo camera device 102, and the illumination device 103. Further, the driving circuit 40 supplies image data of the eyeball 111 acquired by the stereo camera device 102 to the computer system 20 via the input/output interface device 30.

The output device 50 includes a display device such as a flat panel display. Incidentally, the output device 50 may include a printer. The input device 60 generates input data by being operated. The input device 60 includes a keyboard or a mouse for a computer system. Incidentally, the input device 60 may include a touch sensor which is disposed on the display screen of the output device 50 which is the display device. The examinee input unit 70 inputs information indicating whether the examinee can recognize an indicator displayed on the display screen 101S. For example, a button switch or the like is used as the examinee input unit 70. In this configuration, for example, when the examinee determines that the examinee can recognize the indicator, an input signal is transmitted to the computer system 20 by causing the examinee to push a button.

In the present embodiment, the display device 101 and the computer system 20 are separate devices. Incidentally, the display device 101 and the computer system 20 may be integrated. For example, when the line-of-sight detecting device 100 includes a tablet personal computer, the computer system 20, the input/output interface device 30, the driving circuit 40, and the display device 101 may be mounted in the tablet personal computer.

Figure 3:
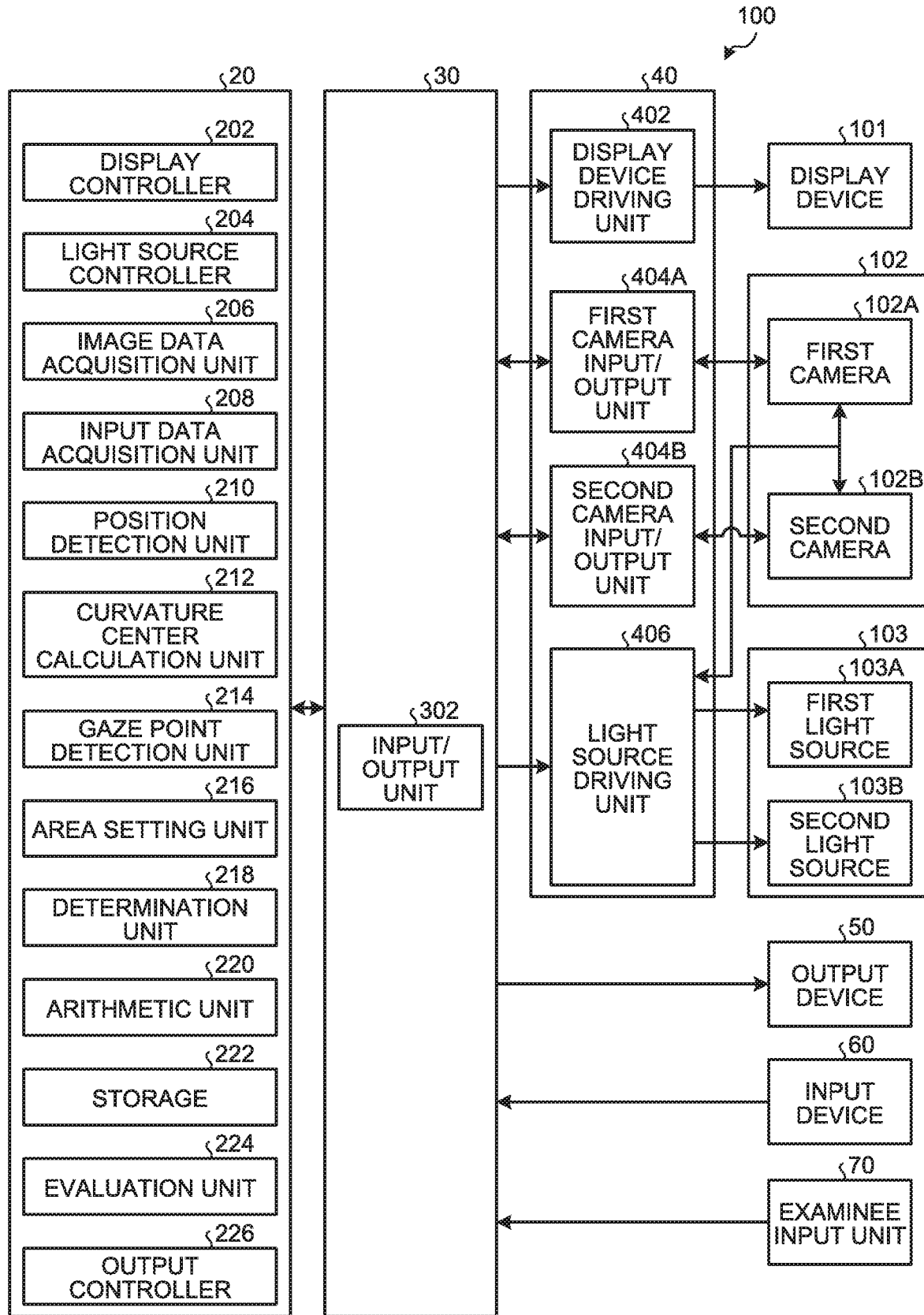
FIG. 3 is a functional block diagram illustrating an example of the line-of-sight detecting device according to the embodiment.

FIG. 3 is a functional block diagram illustrating an example of the line-of-sight detecting device 100 according to the present embodiment. As illustrated in FIG. 3, the input/output interface device 30 includes an input/output unit 302. The driving circuit 40 includes a display device driving unit 402 that generates a drive signal for driving the display device 101 and outputs the drive signal to the display device 101, a first camera input/output unit 404A that generates a drive signal for driving the first camera 102A and outputs the drive signal to the first camera 102A, a second camera input/output unit 404B that generates a drive signal for driving the second camera 102B and outputs the drive signal to the second camera 102B, and a light source driving unit 406 that generates a drive signal for driving the first light source 103A and the second light source 103B and outputs the drive signal to the first light source 103A and the second light source 103B. Further, the first camera input/output unit 404A supplies image data of the eyeball 111 acquired by the first camera 102A to the computer system 20 via the input/output unit 302. The second camera input/output unit 404B supplies image data of the eyeball 111 acquired by the second camera 102B to the computer system 20 via the input/output unit 302.

The computer system 20 controls the line-of-sight detecting device 100. The computer system 20 includes a display controller 202, a light source controller 204, an image data acquisition unit 206, an input data acquisition unit 208, a position detection unit 210, a curvature center calculation unit 212, a gaze point detection unit 214, an area setting unit 216, a determination unit 218, an arithmetic unit 220, a storage 222, an evaluation unit 224, and an output controller 226. The function of the computer system 20 is exhibited by the arithmetic processing device 20A and the storage device 20B.

The display controller 202 displays an indicator for evaluating a visual function of an examinee on the display screen 101S. The display controller 202 displays the indicator at an offset position at which the relative positional relationship with a gaze point of the examinee is constant on the display screen 101S. This indicator is an indicator which is used to determine whether the examinee can recognize the indicator with peripheral vision of the retina.

The light source controller 204 controls the light source driving unit 406 to control operating states of the first light source 103A and the second light source 103B. The light source controller 204 controls the first light source 103A and the second light source 103B such that the first light source 103A and the second light source 103B emit detection light at different timing.

The image data acquisition unit 206 acquires image data of the eyeball 111 of the examinee acquired by the stereo camera device 102 including the first camera 102A and the second camera 102B from the stereo camera device 102 via the input/output unit 302.

The input data acquisition unit 208 acquires input data generated by the input device 60 being operated from the input device 60 via the input/output unit 302.

The position detection unit 210 detects position data of a pupil center based on the image data of the eyeball 111 acquired by the image data acquisition unit 206. Further, the position detection unit 210 detects position data of a corneal reflection center based on the image data of the eyeball 111 acquired by the image data acquisition unit 206. The pupil center is a center of the pupil 112. The corneal reflection center is a center of the corneal reflex image 113. The position detection unit 210 detects the position data of the pupil center and position data of the corneal reflection center for each of the right and left eyeballs 111 of the examinee.

The curvature center calculation unit 212 calculates position data of the corneal curvature center of the eyeball 111 based on the image data of the eyeball 111 acquired by the image data acquisition unit 206.

The gaze point detection unit 214 detects position data of a gaze point of the examinee based on the image data of the eyeball 111 acquired by the image data acquisition unit 206. In the present embodiment, the position data of the gaze point refers to position data of an intersection between a line-of-sight vector of the examinee which is defined in the three-dimensional global coordinate system and the display screen 101S of the display device 101. The gaze point detection unit 214 detects the line-of-sight vector of each of the right and left eyeballs 111 of the examinee based on the position data of the pupil center acquired by the image data of the eyeball 111 and the position data of the corneal curvature center. After the line-of-sight vector has been detected, the gaze point detection unit 214 detects the position data of the gaze point indicating the intersection between the line-of-sight vector and the display screen 101S.

The area setting unit 216 sets a specific area in a part of the display screen 101S of the display device 101.

When the specific area is set on the display screen 101S, the determination unit 218 determines whether the gaze point is present in the specific area based on the position data which is the detection result of the position of the gaze point and outputs determination data. The determination unit 218 determines whether the gaze point is present in the specific area, for example, at constant time intervals. The constant time interval can be set to, for example, a period of the frame synchronization signal (for example, every 50 [msec]) output from the first camera 102A and the second camera 102B.

The arithmetic unit 220 includes a timer that detects a measured time. The arithmetic unit 220 determines whether the examinee has recognized the indicator. The arithmetic unit 220 determines whether the examinee has recognized the indicator based on an input result from the examinee input unit 70. In the present embodiment, when the input result from the examinee input unit 70 has been detected, the arithmetic unit 220 determines that the examinee has recognized the indicator. Further, when the input from the examinee input unit 70 has not been detected, the arithmetic unit 220 determines that the examinee has not recognized the indicator. The arithmetic unit 220 outputs the determination results.

The evaluation unit 224 evaluates a visual function of the examinee and acquires evaluation data. The evaluation data is data for evaluating the visual function of the examinee based on the determination results from the arithmetic unit 220.

The storage 222 stores image data of images which are displayed on the display screen 101S, the determination data output from the determination unit 218, and the evaluation data output from the evaluation unit 224. The images which are displayed on the display screen 101S includes a still image and a moving image. The storage 222 stores multiple pieces of the image data. The storage 222 stores timing data of start and end of displaying the image data. The storage 222 stores data of the position of the indicator which is displayed on the display screen 101S. The data of the position of the indicator may be stored, for example, in correlation with vision of the retina. The storage 222 stores the determination results from the arithmetic unit 220 about whether the examinee has recognized the indicator in correlation with each of the offset positions of the indicator.

The storage 222 stores an evaluation program causing a computer to perform a process of detecting the position of the gaze point of the examinee who observes the display screen on which the image is displayed, a process of displaying the indicator at the offset position at which the relative positional relationship with the gaze point is constant on the display screen based on the detection result of the position of the gaze point, a process of determining whether the examinee has recognized the indicator, and a process of evaluating the visual function of the examinee based on the determination results from the arithmetic unit.

The output controller 226 outputs data to at least one of the display device 101 and the output device 50.

Figure 4:
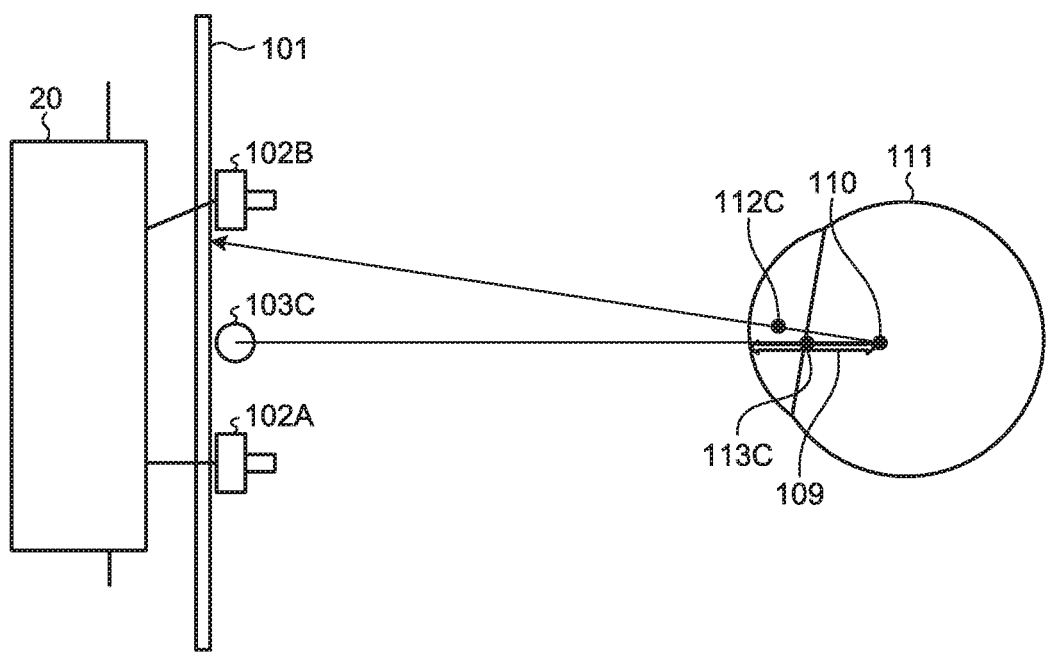
FIG. 4 is a diagram schematically describing a method of calculating position data of a corneal curvature center according to the embodiment.
Figure 5:
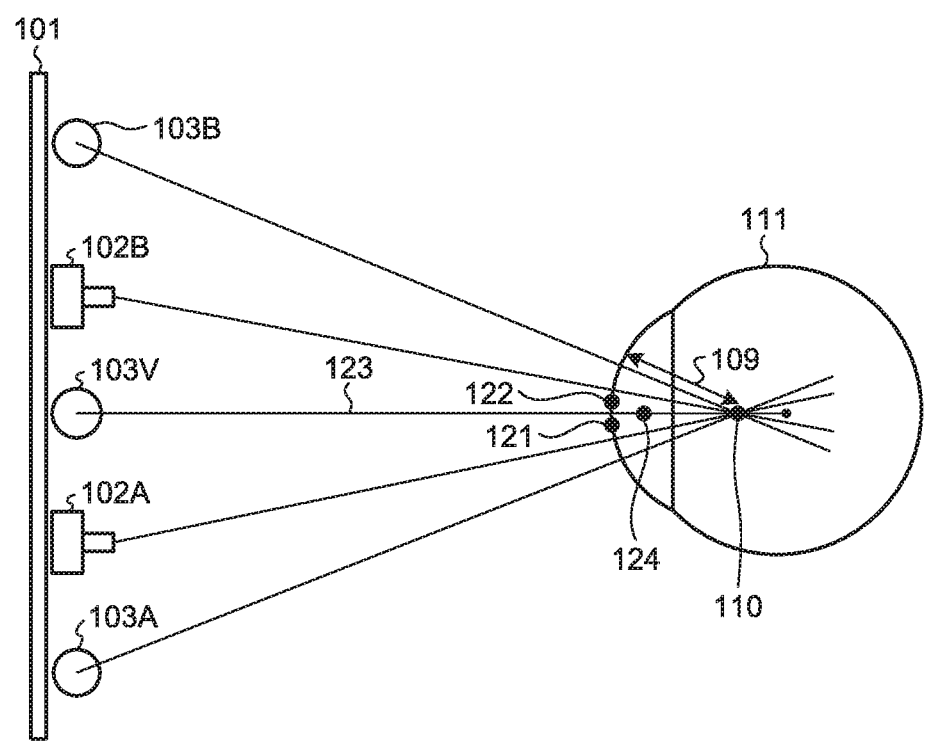
FIG. 5 is a diagram schematically describing a method of calculating position data of the corneal curvature center according to the embodiment.

Next, outline of a process of the curvature center calculation unit 212 according to the present embodiment will be described below. The curvature center calculation unit 212 calculates position data of the corneal curvature center of the eyeball 111 based on the image data of the eyeball 111. FIGS. 4 and 5 are diagrams schematically illustrating a method of calculating the position data of the corneal curvature center 110 according to the present embodiment. FIG. 4 illustrates an example in which the eyeball 111 is illuminated with one light source 103C. FIG. 5 illustrates an example in which the eyeball 111 is illuminated with the first light source 103A and the second light source 103B.

First, the example illustrated in FIG. 4 will be described. The light source 103C is disposed between the first camera 102A and the second camera 102B. A pupil center 112C is a center of the pupil 112. A corneal reflection center 113C is a center of the corneal reflex image 113. In FIG. 4, the pupil center 112C indicates the pupil center when the eyeball 111 is illuminated with one light source 103C. The corneal reflection center 113C indicates the corneal reflection center when the eyeball 111 is illuminated with one light source 103C. The corneal reflection center 113C is present on a straight line that connects the light source 103C to the corneal curvature center 110. The corneal reflection center 113C is positioned at a midpoint between a corneal surface and the corneal curvature center 110. A corneal curvature radius 109 is a distance between the corneal surface and the corneal curvature center 110. Position data of the corneal reflection center 113C is detected by the stereo camera device 102. The corneal curvature center 110 is present on a straight line that connects the light source 103C to the corneal reflection center 113C. The curvature center calculation unit 212 calculates position data at which a distance from the corneal reflection center 113C on the straight line corresponds to a predetermined value as position data of the corneal curvature center 110. The predetermined value is a value which is determined in advance from a general curvature radius value of the cornea and is stored in the storage 222.

Next, the example illustrated in FIG. 5 will be described. In the present embodiment, the first camera 102A, the second light source 103B, the second camera 102B, and the first light source 103A are disposed at positions which are symmetric with respect to a straight line passing through the middle position between the first camera 102A and the second camera 102B. A virtual light source 103V can be considered to be present at the middle position between the first camera 102A and the second camera 102B. A corneal reflection center 121 indicates a corneal reflection center in an image obtained by imaging the eyeball 111 with the second camera 102B. A corneal reflection center 122 indicates a corneal reflection center in an image obtained by imaging the eyeball 111 with the first camera 102A. A corneal reflection center 124 indicates the corneal reflection center corresponding to the virtual light source 103V. Position data of the corneal reflection center 124 is calculated based on position data of the corneal reflection center 121 and position data of the corneal reflection center 122 which are acquired by the stereo camera device 102. The stereo camera device 102 detects the position data of the corneal reflection center 121 and the position data of the corneal reflection center 122 in a three-dimensional local coordinate system which is defined in the stereo camera device 102. Camera calibration based on a stereo calibration method is performed in advance on the stereo camera device 102, and a conversion parameter for converting three-dimensional local coordinate system of the stereo camera device 102 into three-dimensional global coordinate system is calculated. The conversion parameter is stored in the storage 222. The curvature center calculation unit 212 converts the position data of the corneal reflection center 121 and the position data of the corneal reflection center 122 which are acquired by the stereo camera device 102 into position data in the three-dimensional global coordinate system using the conversion parameter. The curvature center calculation unit 212 calculates position data of the corneal reflection center 124 in the three-dimensional global coordinate system based on the position data of the corneal reflection center 121 and the position data of the corneal reflection center 122 which are defined in the three-dimensional global coordinate system. The corneal curvature center 110 is present on a straight line 123 that connects the virtual light source 103V to the corneal reflection center 124. The curvature center calculation unit 212 calculates position data in which a distance from the corneal reflection center 124 on the straight line 123 corresponds to a predetermined value as position data of the corneal curvature center 110. The predetermined value is a value which is determined in advance from a general curvature radius value of the cornea and is stored in the storage 222.

In this way, when there are two light sources, the corneal curvature center 110 is calculated using the same method as the method when there is one light source.

The corneal curvature radius 109 is a distance between the corneal surface and the corneal curvature center 110. Accordingly, the corneal curvature radius 109 is calculated by calculating the position data of the corneal surface and the position data of the corneal curvature center 110.

Figure 6:
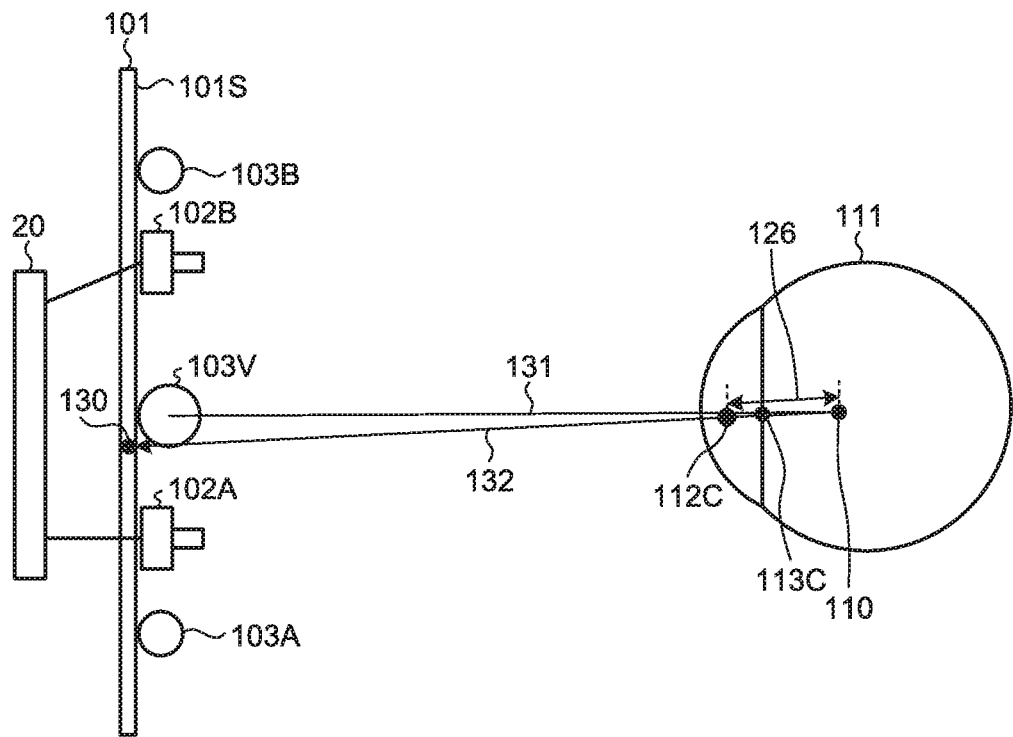
FIG. 6 is a diagram schematically describing an example of a calibration process according to the embodiment.

An example of a line-of-sight detecting method according to the present embodiment will be described below. FIG. 6 is a diagram schematically illustrating an example of a calibration process according to the present embodiment. In the calibration process, a target position 130 is set to cause the examinee to gaze at the target position. The target position 130 is defined in the three-dimensional global coordinate system. In the present embodiment, the target position 130 is set, for example, at a central position of the display screen 101S of the display device 101. Incidentally, the target position 130 may be set at an end position of the display screen 101S. The output controller 226 displays a target image at the set target position 130. A straight line 131 is a straight line that connects the virtual light source 103V to the corneal reflection center 113C. A straight line 132 is a straight line that connects the target position 130 to the pupil center 112C. The corneal curvature center 110 is an intersection between the straight line 131 and the straight line 132. The curvature center calculation unit 212 can calculate the position data of the corneal curvature center 110 based on the position data of the virtual light source 103V, the position data of the target position 130, the position data of the pupil center 112C, and the position data of the corneal reflection center 113C.

Figure 7:
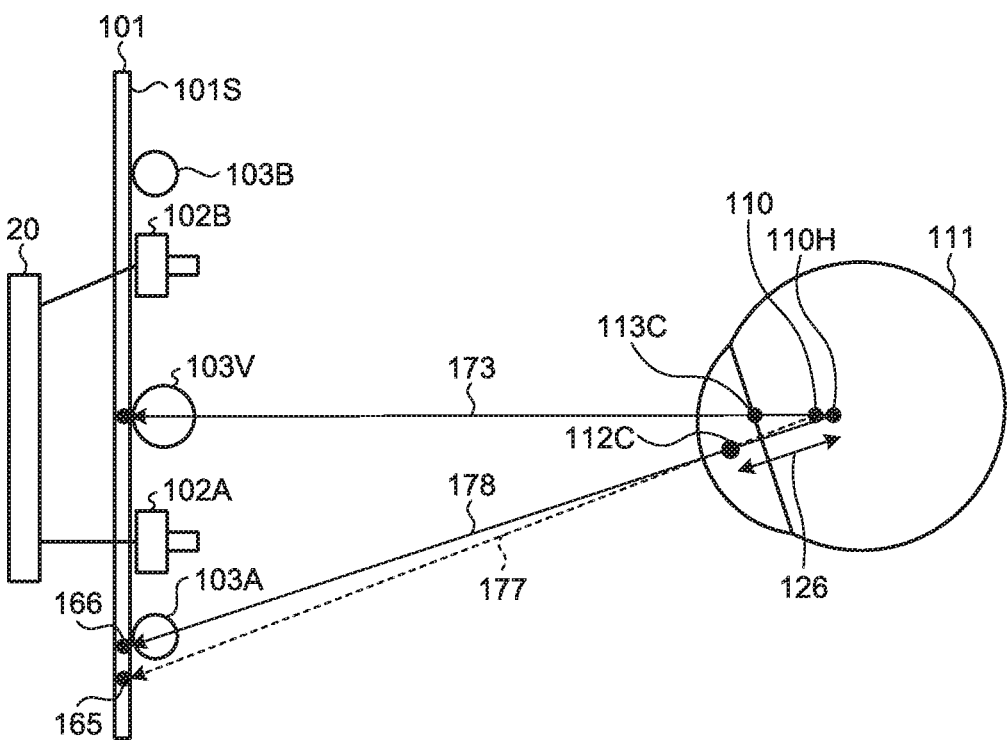
FIG. 7 is a diagram schematically describing an example of a gaze point detecting process according to the embodiment.

A gaze point detecting process will be described below. The gaze point detecting process is performed after the calibration process. The gaze point detection unit 214 calculates a line-of-sight vector of the examinee and position data of the gaze point based on image data of an eyeball 111. FIG. 7 is a diagram schematically illustrating an example of the gaze point detecting process according to the present embodiment. In FIG. 7, the gaze point 165 is a gaze point calculated from the corneal curvature center calculated using a general curvature radius value. A gaze point 166 is a gaze point which is calculated from the corneal curvature center calculated using a distance 126 calculated in the calibration process. The pupil center 112C is a pupil center which is calculated in the calibration process, and the corneal reflection center 113C is a corneal reflection center which is calculated in the calibration process. A straight line 173 is a straight line that connects the virtual light source 103V to the corneal reflection center 113C. The corneal curvature center 110 indicates a position of the corneal curvature center which is calculated from the general curvature radius value. The distance 126 is a distance between the pupil center 112C calculated in the calibration process and the corneal curvature center 110. A corneal curvature center 110H indicates a position of the corrected corneal curvature center which is obtained by correcting the corneal curvature center 110 using the distance 126. The corneal curvature center 110H is calculated based on the facts that the corneal curvature center 110 is located on the straight line 173 and the distance between the pupil center 112C and the corneal curvature center 110 is the distance 126. Accordingly, a line-of-sight 177 which is calculated when using the general curvature radius value is corrected to a line-of-sight 178. Further, the gaze point on the display screen 101S of the display device 101 is corrected from the gaze point 165 to a gaze point 166.

[Evaluation Method]

An evaluation method according to the present embodiment will be described below. In the evaluation method according to the present embodiment, whether or not there is a visual field deficiency due to glaucoma or the like is evaluated as a visual function of the examinee using the line-of-sight detecting device 100.

Figure 8:
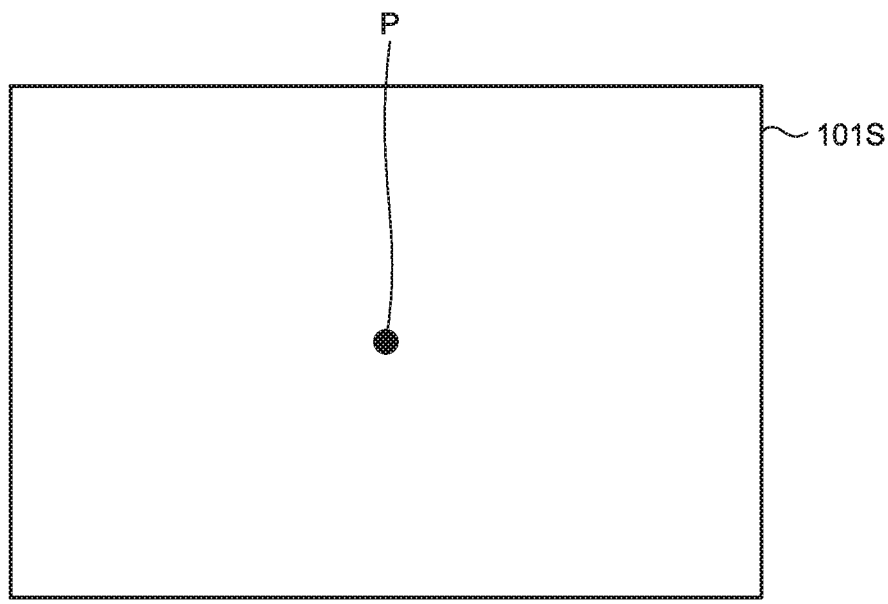
FIG. 8 is a diagram illustrating an example in which an examinee gazes at a display screen.

FIG. 8 is a diagram illustrating an example in which the examinee gazes at the display screen 101S. In FIG. 8, an example of a gaze point P which is displayed as a measurement result on the display screen 101S is illustrated, but the gaze point P is not actually displayed on the display screen 101S. The same applies to the gaze points P in the subsequent drawings thereof. Detection of position data of the gaze point P is performed, for example, in a period of a frame synchronization signal (for example, every 50 [msec]) output from the first camera 102A and the second camera 102B. The first camera 102A and the second camera 102B synchronously capture images. The area setting unit 216 sets a specific area, for example, over the whole display screen 101S. The determination unit 218 determines whether the gaze point P of the examinee is present in the specific area (the display screen 101S).

Figure 9:
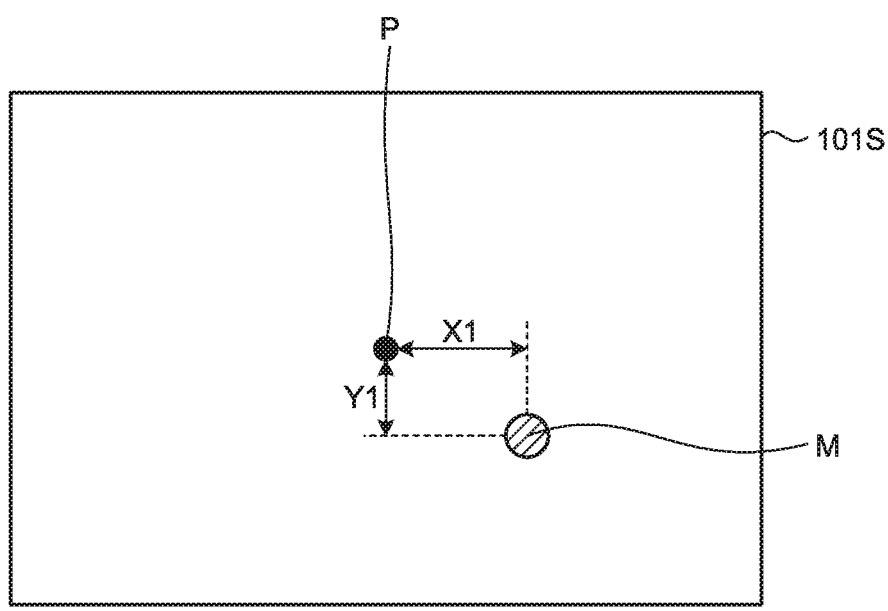
FIG. 9 is a diagram illustrating an example of an indicator which is displayed on the display screen.

FIG. 9 is a diagram illustrating an example of the indicator which is displayed on the display screen 101S. When position data of the gaze point P is acquired and the gaze point P is present on the display screen 101S, the display controller 202 displays the indicator M at an offset position at which the relative positional relationship with the gaze point P is constant as illustrated in FIG. 9. In the present embodiment, the offset position is, for example, a coordinate position which is obtained by adding constant values (for example, X1 for the X coordinate and Y1 for the Y coordinate) to the X coordinate and the Y coordinate of the gaze point P. By setting the offset position in this way, the relative positional relationship between the gaze point P and the indicator M is kept constant. Incidentally, the offset position may be disposed outside the display screen 101S depending on the position of the gaze point P. In this case, the display controller 202 does not display the indicator M.

Figure 10:
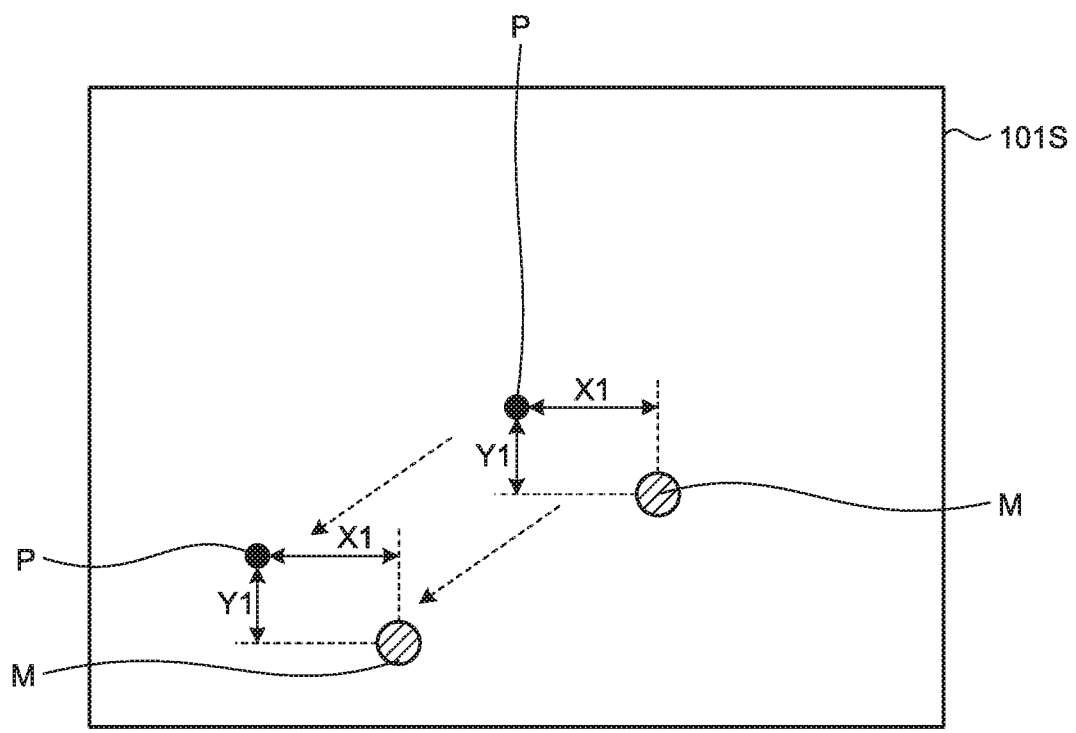
FIG. 10 is a diagram illustrating another example of the indicator which is displayed on the display screen.

FIG. 10 is a diagram illustrating another example of the indicator which is displayed on the display screen 101S. In the present embodiment, the relative positional relationship between the gaze point P and the indicator M is constant as described above. Accordingly, when the examinee moves the gaze point P in a state in which the indicator M is displayed, the display controller 202 calculates the offset position at each time point at which the position data of the gaze point P is detected and displays the indicator M at the offset position. In this case, as illustrated in FIG. 10, the indicator M is displayed to follow the gaze point P in a state in which the relative positional relationship with the gaze point P is maintained.

In the present embodiment, whether or not there is a visual field deficiency is evaluated as the visual function of the examinee by causing the examinee to gaze at the display screen 101S, displaying the indicator M at the offset position at which the relative positional relationship with the gaze point P of the examinee is constant, and determining whether the examinee has recognized the indicator M with the peripheral vision.

Figure 11:
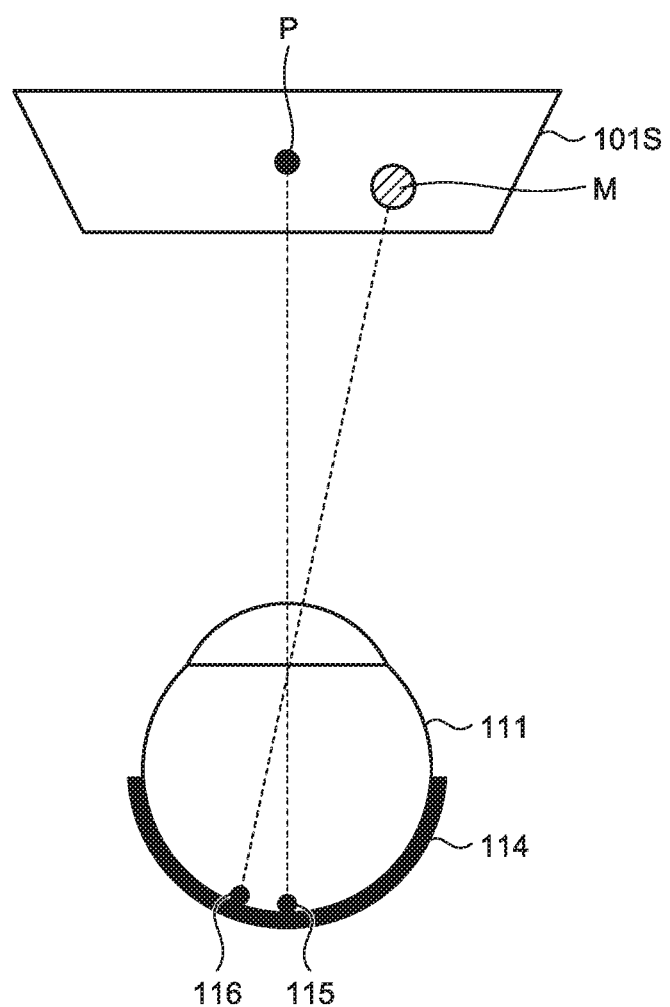
FIG. 11 is a diagram schematically illustrating a principle of an evaluation method according to the embodiment.

FIG. 11 is a diagram schematically illustrating the principle of the evaluation method according to the present embodiment. When the gaze point P of the examinee is present on the display screen 101S as illustrated in FIG. 11, an image corresponding to the gaze point P on the display screen 101S appears at a center of vision 115 of retina 114. At this time, an image of the indicator M appears in peripheral vision 116 of the retina 114. That is, the examinee watches the indicator M with the peripheral vision 116. Accordingly, the examinee who cannot recognize the indicator M in a state in which the examinee gazes at the display screen 101S can be evaluated to have a deficiency of the peripheral vision 116 of the retina 114. In the present embodiment, since the indicator M is displayed to follow the gaze point P in a state in which the relative positional relationship with the gaze point P is maintained, the image of the indicator M can appear in the peripheral vision 116 regardless of the position of the gaze point P while the examinee is gazing at the display screen 101S. Accordingly, the examinee does not have to maintain the gaze point P at any one point and it is possible to perform examination in an examination environment without stress.

For example, when the examinee has recognized the indicator M, the examinee is caused to push the button of the examinee input unit 70. Accordingly, when the input signal from the examinee input unit 70 has been detected, the arithmetic unit 220 determines that the examinee has recognized the indicator M. Further, when the input signal from the examinee input unit 70 has not been detected, the arithmetic unit 220 determines that the examinee has not recognized the indicator M.

Figure 12:
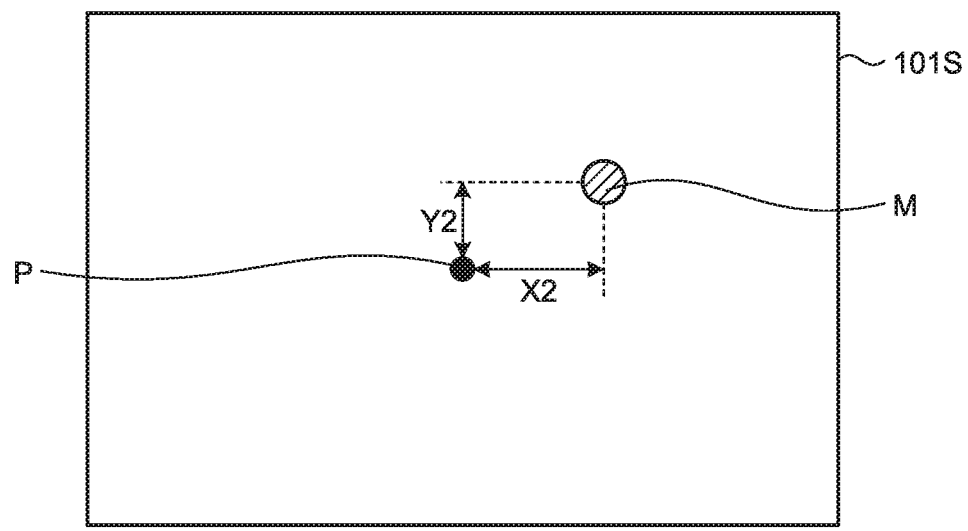
FIG. 12 is a diagram illustrating an example in which the indicator is displayed at a changed position on the display screen.
Figure 13:
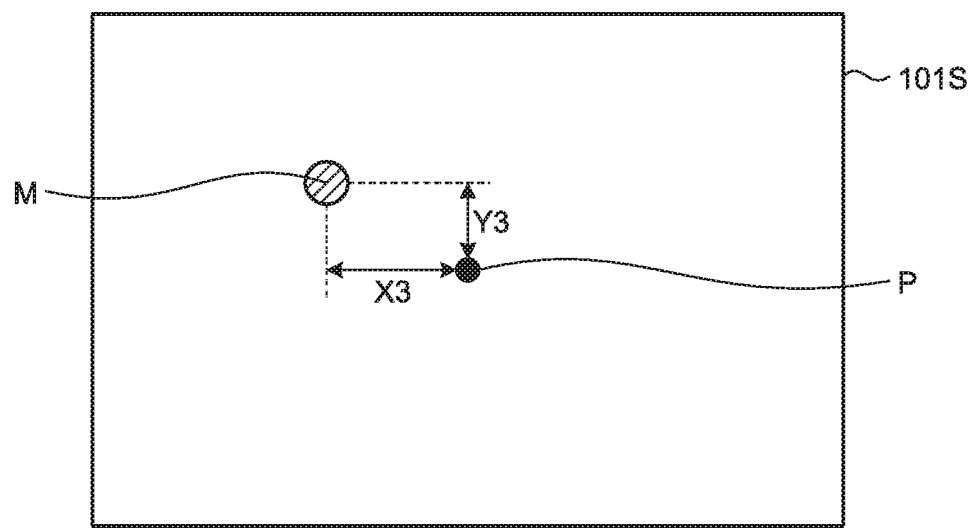
FIG. 13 is a diagram illustrating an example in which the indicator is displayed at a changed position on the display screen.
Figure 14:
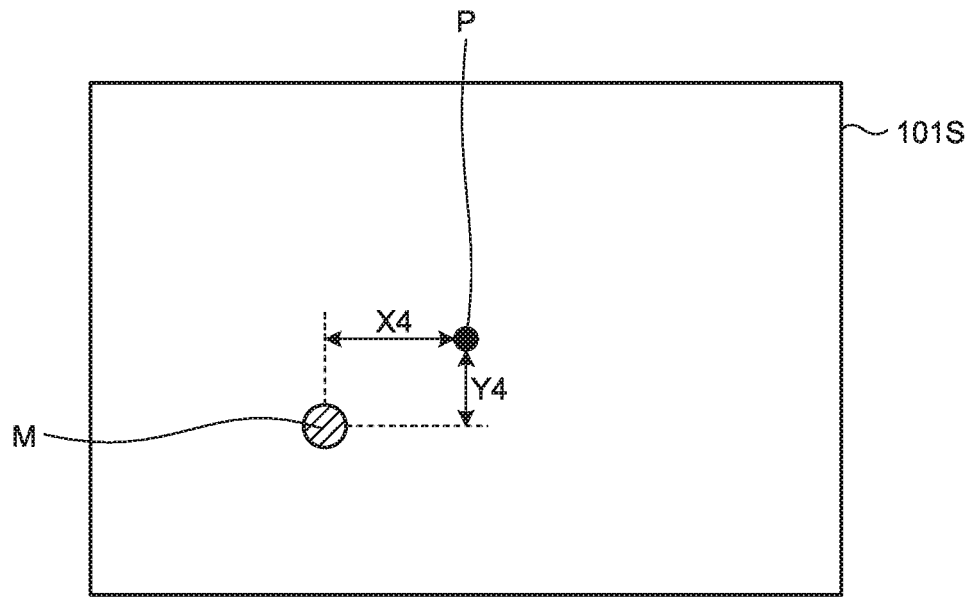
FIG. 14 is a diagram illustrating an example in which the indicator is displayed at a changed position on the display screen.

This examination is performed multiple times while changing the display position of the indicator M. FIGS. 12 to 14 are diagrams illustrating examples in which the indicator M is displayed on the display screen 101S while changing the position thereof. In FIG. 9, the indicator M is displayed at a lower-right position of the gaze point P, and in FIG. 12, the indicator M is displayed at the offset position which is an upper-right position of the gaze point P. In this case, the offset position is a coordinate position which is obtained by adding a constant value X2 for the X coordinate and a constant value Y2 for the Y coordinate to the X coordinate and the Y coordinate of the gaze point P, respectively.

Further, in FIG. 13, the indicator M is displayed at an upper-left position of the gaze point P. In this case, the offset position is a coordinate position which is obtained by adding a constant value X3 for the X coordinate and a constant value Y3 for the Y coordinate to the X coordinate and the Y coordinate of the gaze point P, respectively. Further, in FIG. 14, the indicator M is displayed at a lower-left position of the gaze point P. In this case, the offset position is a coordinate position which is obtained by adding a constant value X4 for the X coordinate and a constant value Y4 for the Y coordinate to the X coordinate and the Y coordinate of the gaze point P, respectively.

Incidentally, the offset positions of the indicator M illustrated in FIGS. 12 to 14 are exemplary and the indicator may be displayed at other offset positions. Further, in the examples illustrated in FIGS. 12 to 14, when the examinee moves the gaze point P, the indicator M is displayed to follow the gaze point P in a state in which the relative positional relationship with the gaze point P is maintained. Accordingly, the examinee can see the indicator M with the peripheral vision 116 regardless of the position of the gaze point P.

In this way, by displaying the indicator M while changing the display position (the offset position) thereof and confirming whether the examinee has recognized the indicator M, it is possible to efficiently evaluate whether or not there is the deficiency of the peripheral vision 116 of the retina 114.

Figure 15:
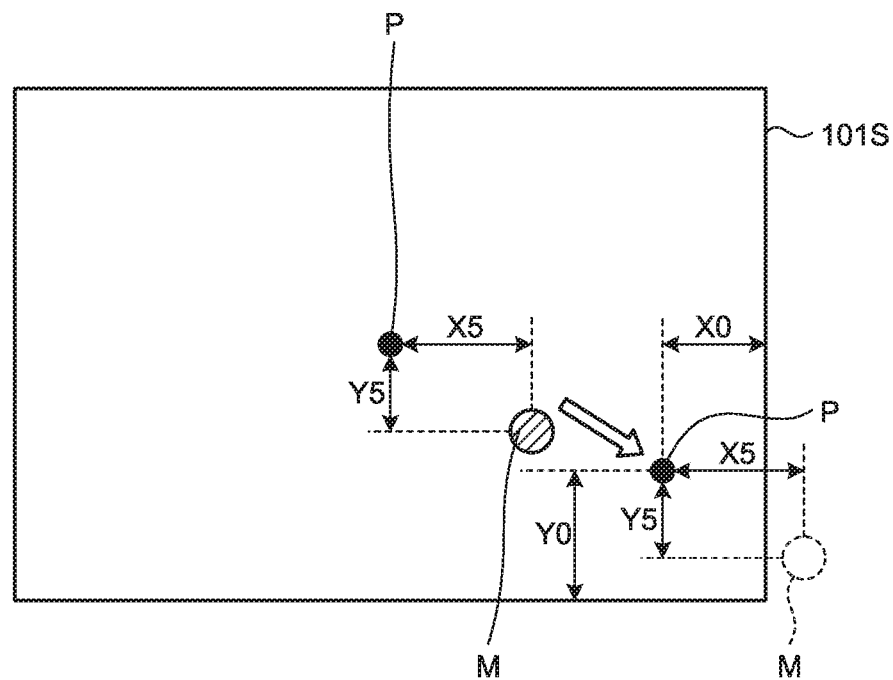
FIG. 15 is a diagram illustrating another example in which the indicator is displayed on the display screen.

When the examination is performed, there is a possibility that the examinee will intend to recognize the indicator M displayed on the display screen 101S with the central vision and move the gaze point P toward the indicator M. FIG. 15 is a diagram illustrating another example in which then indicator M is displayed on the display screen 101S. For example, when the offset position with respect to the gaze point P is present outside the display screen 101S as illustrated in FIG. 15, the indicator M cannot be displayed.

However, in the present embodiment, since the relative positional relationship between the gaze point P and the indicator M is constant, the examinee recognizes the indicator M at almost the same position of the peripheral vision 116 of the retina regardless of the position of the gaze point P. Accordingly, it can be said that the examinee has moved the gaze point P toward the indicator M as illustrated in FIG. 15 just because the examinee has recognized the indicator M. Therefore, in the present embodiment, when the gaze point P moves toward the indicator M and thus the offset position is disposed outside the display screen 101S, the arithmetic unit 220 determines that the examinee has recognized the indicator M.

When this determination is performed, the arithmetic unit 220 first determines whether the gaze point P is present on the display screen 101S and determines whether the indicator M is displayed when the gaze point P is present on the display screen 101S. Thereafter, the arithmetic unit 220 calculates a distance to an edge of the display screen 101S on the indicator M side in each of the X direction and the Y direction based on the coordinate of the gaze point P and the offset position of the indicator M. The arithmetic unit 220 compares the calculated distances (for example, X0 in the X direction and Y0 in the Y direction) with the added values (X5 in the X direction and Y5 in the Y direction) to the X coordinate and the Y coordinate of the gaze point P to set the offset position, and determines whether the added values are less than the calculated distances.

When the added values in the x coordinate and the y coordinate are less than the calculated distances in the x coordinate and the y coordinate, the arithmetic unit 220 determines that the offset position is present on the display screen 101S. When the added values in the x coordinate and the y coordinate are equal to or greater than the calculated distances in the x coordinate and the y coordinate, the arithmetic unit 220 determines that the offset position is present outside the display screen 101S. When a state of "added values<calculated distances" has changed to a state of "added values≥calculated distances," the arithmetic unit 220 determines that the gaze point P has moved toward indicator M and thus the offset position has been disposed outside the display screen 101S, and determines that the examinee has recognized the indicator M.

Figure 16:
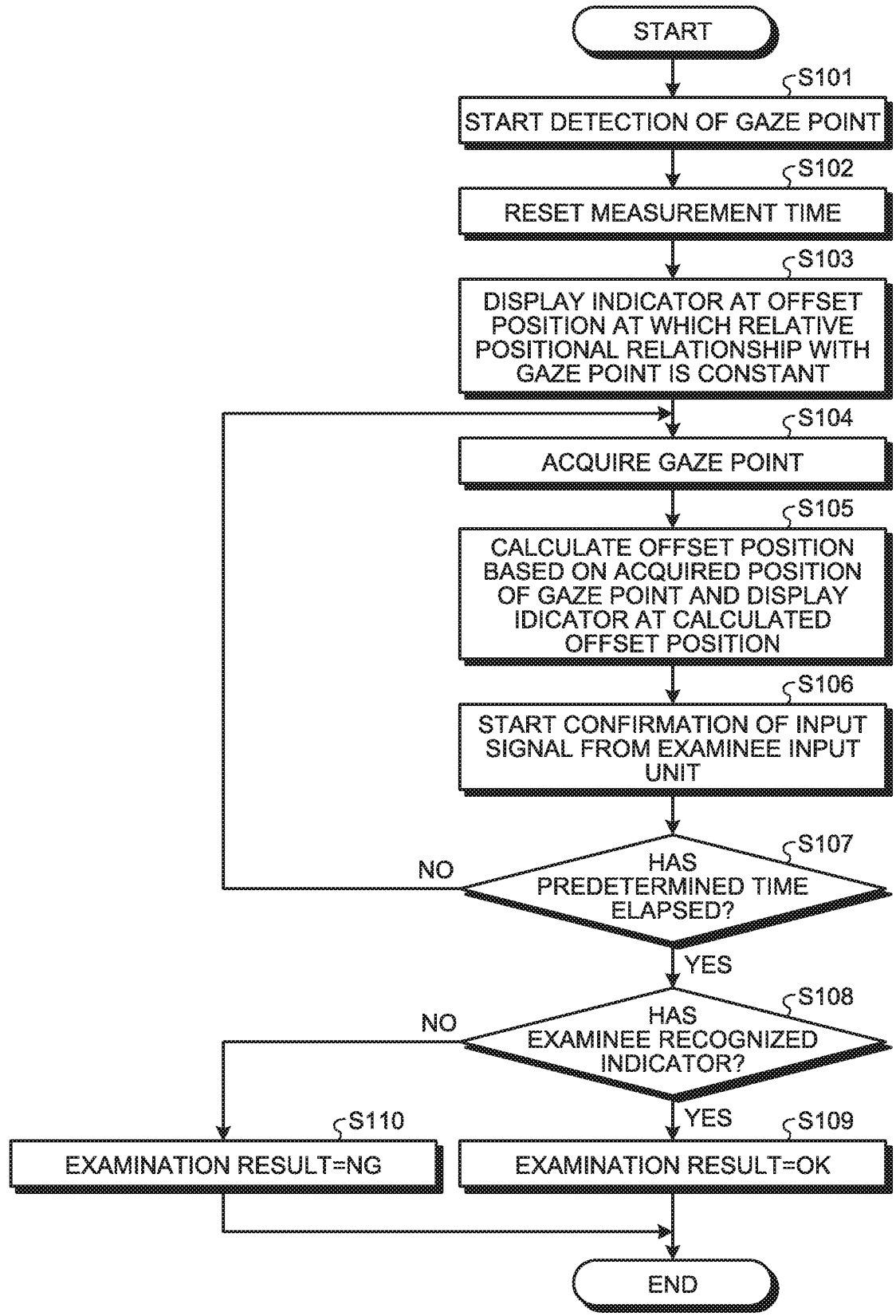
FIG. 16 is a flowchart illustrating an example of a process of determining whether or not the examinee can recognize the indicator.

FIG. 16 is a flowchart illustrating an example of a process of determining whether the examinee has recognized the indicator M. As illustrated in FIG. 16, the gaze point detection unit 214 starts detection of the gaze point P of the examinee (Step S101). After the gaze point P of the examinee has been detected, the area setting unit 216 sets the specific area over almost the entire display screen 101S.

Thereafter, the arithmetic unit 220 resets a measurement time of the timer (Step S102). After the timer has been reset, the display controller 202 displays the indicator M at the offset position at which the relative positional relationship with the gaze point P is constant (Step S103). After the indicator M has been displayed, the gaze point detection unit 214 acquires the gaze point P of the examinee (Step S104). Then, the display controller 202 calculates the offset position based on the position (the coordinates) of the gaze point P acquired in Step S104 and displays the indicator M at the calculated offset position (Step S105). In Step S105, when the position of gaze point P acquired in Step S104 is different from the position of the gaze point P which has been acquired immediately before, the offset position is different from the previous offset position. Accordingly, the display controller 202 displays the indicator M at the new offset position. In this case, the indicator M is displayed to move following movement of the gaze point P.

Thereafter, the arithmetic unit 220 starts confirmation of the input signal from the examinee input unit 70 (Step S106), and determines whether the measurement time of the timer exceeds a predetermined time (Step S107). When the measurement time does not exceed the predetermined time (No in Step S107), the arithmetic unit 220 returns to the process of Step S104.

When the measurement time exceeds the predetermined time (Yes in Step S107), the arithmetic unit 220 determines whether the examinee has recognized the indicator M (Step S108). The arithmetic unit 220 performs the determination of Step S108 based on whether or not there is the input signal from the examinee input unit 70. In this case, when the input signal from the examinee input unit 70 has been detected, the arithmetic unit 220 determines that the examinee has recognized the indicator M. Further, when the input signal from the examinee input unit 70 has not been detected, the arithmetic unit 220 determines that the examinee has not recognized the indicator M. Further, the arithmetic unit 220 may perform the determination of Step S108, for example, based on whether the offset position is disposed outside the display screen 101S by movement of the gaze point P toward the indicator M.

When it is determined that the examinee has recognized the indicator M (Yes in Step S108), the arithmetic unit 220 outputs a message indicating that the examination result is normal (Step S109). On the other hand, when it is determined that the examinee has not recognized the indicator M (No in Step S108), the arithmetic unit 220 outputs a message indicating that the examination result is abnormal (Step S110).

Figure 17:
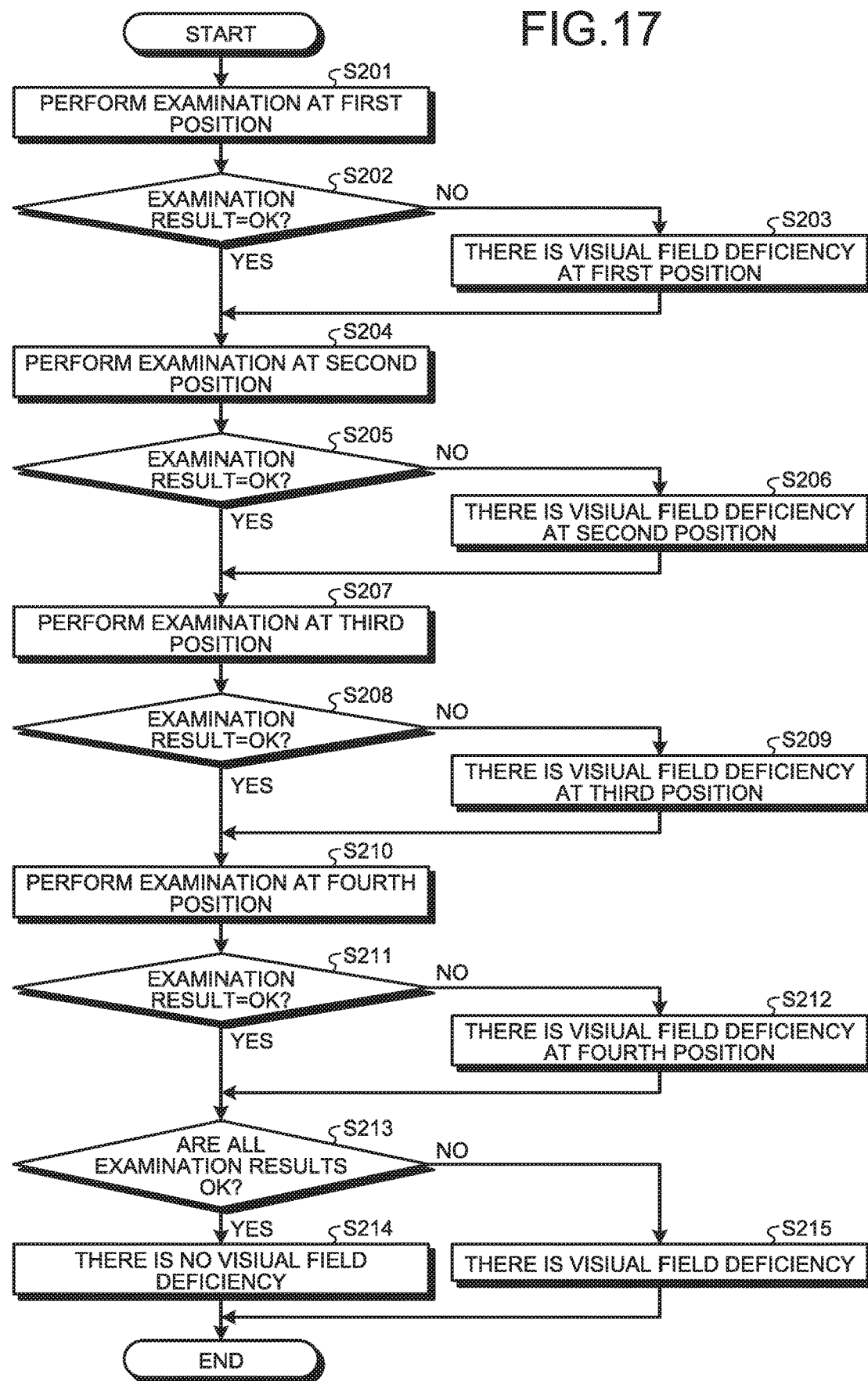
FIG. 17 is a flowchart illustrating an example of the evaluation method according to the embodiment.

FIG. 17 is a flowchart illustrating an example of the evaluation method according to the present embodiment. In the example illustrated in FIG. 17, a case in which the indicator M is displayed at four offset positions illustrated in FIGS. 9, 12, 13, and 14 will be described. In the following description, it is assumed that the offset position of the indicator M illustrated in FIG. 9 is a first position, the offset position of the indicator M illustrated in FIG. 12 is a second position, the offset position of the indicator M illustrated in FIG. 13 is a third position, and the offset position of the indicator M illustrated in FIG. 14 is a fourth position.

As illustrated in FIG. 17, first, in a case in which the indicator M is displayed at the first position, it is determined whether the examinee has recognized the indicator M by performing the process illustrated in FIG. 16 (Step S201). Thereafter, the evaluation unit 224 determines whether the examination result output from the arithmetic unit 220 is normal (Step S202).

When the output result from the arithmetic unit 220 is normal (Yes in Step S202), the evaluation unit 224 performs the subsequent step. When the output result from the arithmetic unit 220 is abnormal (No in Step S202), the evaluation unit 224 determines that there is a visual field deficiency at the first position, stores the determination result in the storage unit 222 (Step S203), and performs the subsequent step.

After Step S202 or S203, in a case in which the indicator M is displayed at the second position, it is determined whether the examinee has recognized the indicator M by performing the process illustrated in FIG. 16 (Step S204).

Thereafter, the evaluation unit 224 determines whether the examination result output from the arithmetic unit 220 is normal (Step S205).

When the output result from the arithmetic unit 220 is normal (Yes in Step S205), the evaluation unit 224 performs the subsequent step. When the output result from the arithmetic unit 220 is abnormal (No in Step S205), the evaluation unit 224 determines that there is a visual field deficiency n at the second position, stores the determination result in the storage unit 222 (Step S206), and performs the subsequent step.

After Step S205 or S206, in a case in which the indicator M is displayed at the third position, it is determined whether the examinee has recognized the indicator M by performing the process illustrated in FIG. 16 (Step S207). Thereafter, the evaluation unit 224 determines whether the examination result output from the arithmetic unit 220 is normal (Step S208).

When the output result from the arithmetic unit 220 is normal (Yes in Step S208), the evaluation unit 224 performs the subsequent step. When the output result from the arithmetic unit 220 is abnormal (No in Step S208), the evaluation unit 224 determines that there is a visual field deficiency at the third position, stores the determination result in the storage unit 222 (Step S209), and performs the subsequent step.

After Step S208 or S209, in a case in which the indicator M is displayed at the fourth position, it is determined whether the examinee has recognized the indicator M by performing the process illustrated in FIG. 16 (Step S210). Thereafter, the evaluation unit 224 determines whether the examination result output from the arithmetic unit 220 is normal (Step S211).

When the output result from the arithmetic unit 220 is normal (Yes in Step S211), the evaluation unit 224 performs the subsequent step. When the output result from the arithmetic unit 220 is abnormal (No in Step S211), the evaluation unit 224 determines that there is a visual field deficiency at the fourth position, stores the determination result in the storage unit 222 (Step S212), and performs the subsequent step.

After Step S211 or S212, the evaluation unit 224 determines whether all the examination results are normal (Step S213). When it is determined that all the examination results are normal (Yes in Step S213), the evaluation unit 224 outputs an evaluation result indicating that there is no visual field deficiency (Step S214). When at least one of the examination results is abnormal (No in Step S213), the evaluation unit 224 outputs an evaluation result indicating that the examinee has a visual field deficiency (Step S215). In Step S215, the evaluation unit 224 may evaluate at which position there is a visual field deficiency based on the determination results stored in the storage unit 222.

As described above, the line-of-sight detecting device 100 according to the present embodiment includes: a display screen 101S configured to displays images; a gaze point detection unit 214 configured to detect a position of a gaze point P of an examinee who observes the display screen 101S; a display controller 202 configured to display an indicator M at an offset position having a predetermined relative positional relationship with the gaze point P on the display screen 101S based on a detection result of the position of the gaze point P; an arithmetic unit 220 configured to determine whether the examinee has recognized the indicator M; and an evaluation unit 224 configured to evaluate a visual function of the examinee based on a determination result from the arithmetic unit 220, wherein the arithmetic unit 220 is further configured to determine that the examinee has recognized the indicator M when the gaze point P moves toward the indicator M and thus the offset position is located outside the display screen 101S.

The evaluation method according to the present embodiment includes: detecting a position of a gaze point P of an examinee who observes a display screen 101S that displays images; displaying an indicator M at an offset position having a predetermined relative positional relationship with the gaze point P on the display screen 101S based on a detection result of the position of the gaze point P; determining whether the examinee has recognized the indicator M; evaluating a visual function of the examinee based on a determination result of the recognition of the indicator M; and determining that the examinee has recognized the indicator M when the gaze point P moves toward the indicator M and thus the offset position is located outside the display screen 101S.

The non-transitory storage medium that stores the evaluation program according to the present embodiment causes a computer to perform: detecting a position of a gaze point P of an examinee who observes a display screen 101S that displays images; displaying an indicator M at an offset position having a predetermined relative positional relationship with the gaze point P on the display screen 101S based on a detection result of the position of the gaze point P; determining whether the examinee has recognized the indicator M; evaluating a visual function of the examinee based on a determination result of the recognition of the indicator M; and determining that the examinee has recognized the indicator M when the gaze point P moves toward the indicator M and thus the offset position is located outside the display screen 101S.

According to this configuration, since the indicator M is displayed at the offset position having a constant relative positional relationship with the gaze point P, the image of the indicator M can be made to appear with the peripheral vision 116 regardless of the position of the gaze point P while the examinee is gazing at the display screen 101S. Accordingly, since the examinee does not have to maintain the gaze point P at a certain point, it is possible to perform evaluation with high accuracy. It is also possible to perform examination in an examination environment in which the examinee is free of stress.

In the line-of-sight detecting device 100 according to the present embodiment, the arithmetic unit 220 determines that the examinee has recognized the indicator M, when the gaze point P moves toward the indicator M and thus the offset position is displayed outside the display screen 101S. Accordingly, it is possible to efficiently determine whether the examinee has recognized the indicator M.

The line-of-sight detecting device 100 according to the present embodiment further includes the examinee input unit 70 to which a recognition state of the indicator M by the examinee is input, and the arithmetic unit 220 determines whether the examinee has recognized the indicator M based on the input result to the examinee input unit 70. Accordingly, it is possible to easily perform the evaluation with high accuracy.

The technical scope of the application is not limited to the above-mentioned embodiment and can be appropriately modified without departing from the gist of the application. For example, in the above-mentioned embodiment, an example with configuration in which the display screen 101S has a rectangular shape is described, but the application is not limited thereto. For example, the display screen 101S may have a shape curved such that a distance from the examinee is within a predetermined range.

According to the application, it is possible to provide an evaluation device, an evaluation method, and a non-transitory storage medium that can perform evaluation with higher accuracy.

Although the application has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An evaluation device comprising:
a display screen configured to display images;
a gaze point detection unit configured to detect a position of a gaze point of an examinee who observes the display screen;
a display controller configured to display an indicator at an offset position having a predetermined relative positional relationship with the gaze point on the display screen based on a detection result of the position of the gaze point;
an arithmetic unit configured to determine whether the examinee has recognized the indicator; and
an evaluation unit configured to evaluate a visual function of the examinee based on a determination result from the arithmetic unit, wherein
the arithmetic unit is further configured to determine that the examinee has recognized the indicator, in a case wherein
the examinee intends to recognize the indicator displayed on the display screen with a central vision of the examinee;
the gaze point moves toward the indicator having the predetermined relative positional relationship with the gaze point; and
a position of the indicator moves in the display screen to follow a movement of the position of the gaze point and comes to be located outside the display screen and thus the indicator cannot be displayed on the display screen.

2. The evaluation device according to claim 1, further comprising an examinee input unit to which a recognition state of the indicator by the examinee is input,
wherein the arithmetic unit determines whether the examinee has recognized the indicator based on an input result to the examinee input unit.

3. An evaluation method comprising:
detecting a position of a gaze point of an examinee who observes a display screen that displays images;
displaying an indicator at an offset position having a predetermined relative positional relationship with the gaze point on the display screen based on a detection result of the position of the gaze point;
determining whether the examinee has recognized the indicator;
evaluating a visual function of the examinee based on a determination result of the recognition of the indicator; and
determining that the examinee has recognized the indicator, in a case wherein
the examinee intends to recognize the indicator displayed on the display screen with a central vision of the examinee;

the gaze point moves toward the indicator having the predetermined relative positional relationship with the gaze point; and a position of the indicator moves in the display to follow a movement of the position of the gaze point and comes to be located outside the display screen and thus the indicator cannot be displayed on the display screen.

4. A non-transitory storage medium that stores an evaluation program causing a computer to perform:

- detecting a position of a gaze point of an examinee who observes a display screen that displays images;
- displaying an indicator at an offset position having a predetermined relative positional relationship with the gaze point on the display screen based on a detection result of the position of the gaze point;
- determining whether the examinee has recognized the indicator;
- evaluating a visual function of the examinee based on a determination result of the recognition of the indicator; and
- determining that the examinee has recognized the indicator, in a case wherein
  - the examinee intends to recognize the indicator displayed on the display screen with a central vision of the examinee;
  - the gaze point moves toward the indicator having the predetermined relative positional relationship with the gaze point; and
  - a position of the indicator moves in the display screen to follow a movement of the position of the gaze point and comes to be located outside the display screen and thus the indicator cannot be displayed on the display screen.

* * * * *